United States Patent [19]
Watanabe et al.

[11] Patent Number: 5,731,293
[45] Date of Patent: Mar. 24, 1998

[54] ESCULETIN DERIVATIVES, METHOD FOR MANUFACTURE THEREOF, AND PHARMACEUTICAL COMPOSITION

[75] Inventors: Koju Watanabe; Koichi Niimura, both of Saitama; Toru Yamazaki; Hiroshi Maruoka, both of Tokyo, all of Japan

[73] Assignee: Kureha Chemical Industry Co., Ltd., Tokyo, Japan

[21] Appl. No.: 580,364

[22] Filed: Dec. 28, 1995

[30] Foreign Application Priority Data

Dec. 28, 1994 [JP] Japan .................. 6-340016

[51] Int. Cl.⁶ .............. A61K 31/70; A61K 31/35; C07H 15/24; C07D 313/06
[52] U.S. Cl. ............... 514/27; 514/23; 514/25; 514/237.5; 514/451; 514/457; 536/17.2; 536/17.9; 536/18.1; 536/53; 544/151; 549/269; 549/273; 549/289; 549/294
[58] Field of Search ............... 549/269, 273, 549/289, 294; 514/457, 27, 237.5, 23, 25, 451; 536/53, 17.2, 17.9, 18.1; 544/151

[56] References Cited

FOREIGN PATENT DOCUMENTS

| | | |
|---|---|---|
| 0614896 | 9/1994 | European Pat. Off. . |
| 46007686 | 1/1968 | Japan . |
| 47-14570 | 5/1972 | Japan . |

OTHER PUBLICATIONS

Chemical Abstracts, vol. 83, No. 27, 1975, Abstract #193007c, "Potential anticancer agents. IX. Synthesis of new urethane type nitrogen mustards from benzo–and naphthopyrans." Dragota et al.

*Primary Examiner*—Elli Peselev
*Attorney, Agent, or Firm*—Sughrue, Mion, Zinn, Macpeak & Seas, PLLC

[57] ABSTRACT

A compound of the formula (I):

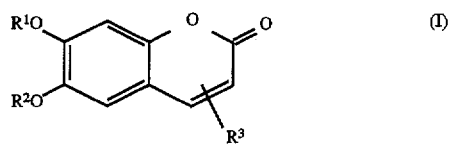

wherein $R^1$ and $R^2$ are, independently, —CON($R^4$)$R^5$, or a monosaccharide, or acylated monosaccharide group, with the proviso that at least one of $R^1$ and $R^2$ is —CON($R^4$)$R^5$, and $R^4$ and $R^5$ are, independently, a hydrogen atom, or a hydroxyl, alkyl, aryl, or aralkyl group, or $R^4$ and $R^5$ together with the nitrogen atom attached thereto form a 3- to 7-membered saturated cycloaliphatic amino group, and $R^3$ is a hydrogen atom, or a hydroxyl, alkyl, aryl, aralkyl, or —COOR$^8$ group, and $R^3$ is at 3- or 4-position, and $R^8$ is a hydrogen atom or an alkyl group, or a salt thereof is disclosed. The compound has a function to inhibit a matrix metalloproteinase.

16 Claims, 2 Drawing Sheets

Fig. 1

The Amount of MMP-1 in culture media (%)

a: Control b: IL-1α c: IL-1α + 33μM esculetin derivative (Ib-2) of the present invention d: IL-1α + 330μM esculetin derivative (Ib-2) of the present invention

Fig. 2

ESCULETIN DERIVATIVES, METHOD FOR MANUFACTURE THEREOF, AND PHARMACEUTICAL COMPOSITION

BACKGROUND OF THE INVENTION

1. Field of the Invention

The present invention relates to a novel esculetin derivative, a method for manufacture thereof, and a pharmaceutical composition, particularly a matrix metalloproteinase inhibitor, comprising the esculetin derivative.

2. Description of the Related Art

Metalloenzymes which degrade protein components in the extracellular matrix are generically called matrix metalloproteinases (hereinafter, sometimes referred to as MMPs). The MMPs are generally devided into four groups: a collagenase group, such as interstitial collagenase (MMP-1) and leukocyte collagenase (MMP-8); a gelatinase/IV type collagenase group, such as gelatinase A (MMP-2) and gelatinase B (MMP-9); a stromelysin group, such as stromelysin-1 (MMP-3), stromelysin-2 (MMP-10), and stromelysin-3 (MMP-11); and the other group, such as matrilysin (MMP-7).

Recently, relation between the MMPs and various types of diseases has become clear. For example, the possibility that the MMPs are deeply involved in pathologic tissues of (a) synovial membrane and articular cartilage tissues of rheumatoid arthritis or osteoarthritis, (b) corneal ulcer, (c) wound healing, (d) granuloma, (e) periodontosis, (f) vesicular exanthem, (g) pulmonary emphysema, (h) glomerular nephritis, (i) pathologic bone resorption, and (j) infiltration and cancer metastasis is reported by Okada ["Matrix Metalloproteinases in Inflammation", Soshiki Baiyo (Tissue Culture), 19, (11), 386–390, 1993). For example, it is confirmed at the gene and protein level that production of the MMPs increases in the tumor tissues or inflammatory sites. Accordingly, substances which can inhibit production or activity of the MMPs are expected to show some effective function against these various types of diseases described above.

Known matrix metalloproteinase inhibitors include peptides having the structure similar to that of the substrates disclosed in, for example, Japanese National Publication (Kohyo) No. 4-501423, or hydroxamic acids disclosed in, for example, Japanese Unexamined Patent Publication (Kokai) No. 6-256293. However, they have disadvantages in that they are subject to hydrolysis and thus, it is hard to maintain efficacy thereof.

SUMMARY OF THE INVENTION

Accordingly, the object of the present invention is to provide a novel compound which is different from conventional matrix metalloproteinase inhibitors such as peptide compounds, has improved affinity and local retention to the target tissues, and can sustain inhibitory activity on MMP production.

Other objects and advantageous effects of the present invention will be apparent from the following description.

The present invention relates to an esculetin derivative of the formula (I):

wherein $R^1$ and $R^2$ are, independently, —$CON(R^4)R^5$, or a monosaccharide, or acylated monosaccharide group, with the proviso that at least one of $R^1$ and $R^2$ is —$CON(R^4)R^5$, and $R^4$ and $R^5$ are, independently, a hydrogen atom, or a hydroxyl, alkyl, aryl, or aralkyl group, or $R^4$ and $R^5$ together with the nitrogen atom attached thereto form a 3- to 7-membered saturated cycloaliphatic amino group, and $R^3$ is a hydrogen atom, or a hydroxyl, alkyl, aryl, aralkyl, or —$COOR^8$ group, and $R^3$ is at 3- or 4-position, and $R^8$ is a hydrogen atom or an alkyl group, or a salt thereof.

Further, the present invention relates to a process for manufacturing the esculetin compound of the formula (I) or the salt thereof comprising reacting a compound of the formula (XI)

wherein $R^3$ has the same meaning as above, a compound of the formula (II)

wherein $R^3$ has the same meaning as above and $R^6$ is a monosaccharide group or acylated monosaccharide group, or a compound of the formula (II')

wherein $R^3$ and $R^6$ have the same meanings as above, with a compound of the formula (X)

$$R^5(R^4)NCOX \qquad (X)$$

wherein $R^4$ and $R^5$ have the same meanings and X is a halogen atom.

Further, the present invention also relates to a pharmaceutical composition, particularly a matrix metalloproteinase inhibitor, comprising the esculetin derivative of the formula (I) or a pharmaceutically acceptable salt thereof.

BRIEF DESCRIPTION OF THE DRAWINGS

In FIG. 1, the percentages of the amounts of MMP-1 produced and released by adding both IL-1α and the compound to be tested as compared to the amounts of MMP-1 produced by adding only IL-1α are shown.

DETAILED DESCRIPTION OF THE PREFERRED EMBODIMENTS

The term "monosaccharide group" used herein means a group formed by removing 1-hydroxyl group from a monosaccharide compound.

These monosaccharide compounds are not only compounds of the formula $(CH_2O)n$ (wherein n is an integer of 3 or more), but also include the derivatives thereof, for example, deoxy sugars, aminosugars, saccharic acids, sugar alcohols, or the like; esters, such as sulfates or phosphates; salts of these esters; ethers such as methylether; and salts of amino sugars, or saccharic acids, or the like. Concrete examples of the monosaccharides are mentioned in Takashi Mizuno and Kazutoshi Nishizawa ed., "Zukai Tositsukagaku Binran (Illustrated Carbohydrate Chemistry Handbook)", published by Kyoritsu Shuppan Co., Japan (1971).

Preferred monosaccharides are pentoses and hexoses. Preferred examples of pentoses are arabinose, xylose, ribose, or deoxyribose. Preferred examples of hexoses are mannose, allose, altrose, talose, glucose, galactose, idose, gulose, fructose, rhamnose, fucose, glucosamine, N-acylglucosamine, galactosamine, N-acylgalactosamine, N-acylmuramic acid, glucuronic acid, gulonic acid, iduronic acid, ascorbic acid, mannitol, or sorbitol. Further, possible esters such as sulfates or phosphates, and salts of these monosaccharides are also included.

More preferred monosaccharides are mannose, glucose, galactose, fructose, rhamnose, fucose, glucosamine, N-acylglucosamine, galactosamine, N-acylgalactosamine, or glucuronic acid. Further, possible esters such as sulfates or phosphates, and salts of these monosaccharides are also included.

The most preferred monosaccharides are glucose, galactose, rhamnose, N-acylglucosamine, N-acylgalactosamine, or glucuronic acid. Further, possible esters such as sulfates or phosphates, and salts of these monosaccharides are also included.

The acyl group of the N-acylsaccharide is preferably an acyl group of 2 to 20 carbon atoms, more preferably an acyl group of 2 to 5 carbon atoms, most preferably an acetyl group.

The acylated monosaccharide group in the esculetin derivatives of the present invention means a monosaccharide group wherein at least one of hydroxyl groups is acylated. The acyl group in the acylated monosaccharide group is preferably an acyl group of 2 to 20 carbon atoms, more preferably an acyl group of 2 to 6 carbon atoms, most preferably an acetyl or pivaloyl group. The acylated monosaccharide group wherein one or all of the hydroxyl groups are acetylated is preferable, and the acylated monosaccharide group wherein all of the hydroxyl groups are acetylated is particularly preferable. In the case of acylation for a hydroxyl group in a hexose group, acylation of 6-hydroxyl group is preferable, and a hexose group wherein 6-hydroxyl group is pivaloylated is most preferable.

The monosaccharide and acylated monosaccharide groups in the esculetin derivatives of the present invention may have D-configuration or L-configuration, and pyranose structure or furanose structure.

In the esculetin derivatives of the present invention, the esculetin moiety is bonded with the monosaccharide or acylated monosaccharide groups via a glycoside bond. The configuration of 1-position of the glycoside may be an α-anomer or a β-anomer.

In —$CON(R^4)R^5$ in the esculetin derivatives of the present invention, $R^4$ and $R^5$ are, independently, a hydrogen atom, or a hydroxyl, alkyl, aryl, or aralkyl group, or $R^4$ and $R^5$ together with the nitrogen atom attached thereto may form a 3- to 7-membered saturated cycloaliphatic amino group.

The alkyl group as the above-mentioned $R^4$ and $R^5$, is preferably an aliphatic alkyl group, more preferably a lower alkyl group of 1 to 4 carbon atoms, such as, methyl, ethyl, n-propyl, isopropyl, n-butyl, isobutyl, s-butyl, or t-butyl group. Methyl group or ethyl group is particularly preferable, and methyl group is the most preferable. These alkyl groups may be substituted by one or more substituents, for example, halogen atom, such as a fluorine, chlorine, bromine, or iodine atom, and/or a hydroxyl group. As concrete examples of the substituted alkyl groups, a hydroxymethyl, trifluoromethyl, or chloroethyl group is preferable.

The aryl group as $R^4$ and $R^5$ is preferably an aryl group of 6 to 12 carbon atoms, for example, phenyl, naphthyl, or biphenyl group. These aryl groups may be substituted by one or more substituents, for example, a lower alkyl group of 1 to 4 carbon atoms, a halogen atom, such as a fluorine, chlorine, bromine, or iodine atom, and/or a hydroxyl group. Phenyl or substituted phenyl group is preferable.

Further, the aralkyl group as $R^4$ and $R^5$ is preferably a lower alkyl group of 1 to 4 carbon atoms substituted with an aryl group of 6 to 12 carbon atoms, for example, a benzyl, phenylethyl, phenylpropyl, or phenylbutyl group. The aryl moiety of the aralkyl group may also be substituted by one or more substituents, for example, a lower alkyl group of 1 to 4 carbon atoms, a halogen atom, such as a fluorine, chlorine, bromine, or iodine atom, and/or a hydroxyl group. Benzyl or substituted benzyl group is preferable.

The 3- to 7-membered saturated cycloaliphatic amino group formed from above-mentioned $R^4$ and $R^5$ is an alkyleneamino group wherein one or more carbon atoms may be optionally replaced by one or more heteroatoms such as nitrogen, oxygen and/or sulfur atoms, for example, 1-azetidinyl ($NC_3H_6$), 1-pyrrolidinyl ($NC_4H_8$), piperidino ($NC_5H_{10}$), morpholino ($NC_4H_8O$), thiomorpholino ($NC_4H_8S$), or 1-piperazinyl ($NC_4H_8NH$).

$R^3$ in the esculetin derivative of the present invention is a hydrogen atom, or a hydroxyl, alkyl, aryl, aralkyl, or —$COOR^8$ group wherein $R^8$ is a hydrogen atom or an alkyl group, and bound to 3- or 4-carbon atom in the coumarin ring. Hereinafter, the esculetin compound having the substituent at 3-position of the coumarin ring is sometimes referred to as a 3-substituted esculetin compound and the esculetin compound having the substituent group at 4-position of the coumarin ring sometimes is referred to as a 4-substituted esculetin compound.

The —$COOR^8$ groups as $R^3$ is a carboxyl group or an alkyl ester group thereof. The alkyl group as $R^8$ is preferably an aliphatic alkyl group, more preferably a lower alkyl group of 1 to 4 carbon atoms, such as, a methyl, ethyl, n-propyl, isopropyl, n-butyl, isobutyl, s-butyl, or t-butyl group.

The alkyl group as $R^3$ is preferably an aliphatic alkyl group, more preferably a lower alkyl group of 1 to 4 carbon atoms, such as, a methyl, ethyl, n-propyl, isopropyl, n-butyl, isobutyl, s-butyl, or t-butyl group. Methyl group or ethyl group is particularly preferable, and methyl group is the most preferable.

The aryl group as $R^3$ is preferably an aryl group of 6 to 12 carbon atoms, for example, a phenyl, naphthyl, or biphenyl group. These aryl groups may be substituted by one or more substituents, for example, a lower alkyl group of 1 to 4 carbon atoms, a halogen atom, such as a fluorine, chlorine, bromine, or iodine atom, and/or a hydroxyl group. Phenyl or substituted phenyl group is preferable.

Further, the aralkyl group as $R^3$ is preferably a lower alkyl group of 1 to 4 carbon atoms substituted with an aryl group of 6 to 12 carbon atoms, for example, a benzyl, phenylethyl, phenylpropyl, or phenylbutyl group. The aryl moiety of the aralkyl group may also be substituted by one or more substituents, for example, a lower alkyl group of 1 to 4 carbon atoms, a halogen atom, such as a fluorine, chlorine, bromine, or iodine atom, and/or a hydroxyl group. Benzyl or substituted benzyl group is preferable.

The salts of the esculetin derivatives of the present invention are formed in a sulfate or phosphate ester of the sugar, at a carboxylic group of saccharic acid such as uronic acid, at an amino group of amino sugar, at the 3- or 4-hydroxyl group of the esculetin structure, at the nitrogen atom of the alkyleneamino group, or the like. For example, salts with inorganic or organic acids, or salts with inorganic or organic bases are included, and the pharmaceutically acceptable salts are preferable. As the acid addition salts, there may be mentioned, for example, hydrochlorides, sulfates, methanesulfonates, or p-toluenesulfonates and, further, salts with dicarboxylic acids, such as oxalic, malonic, succinic, maleic, or fumaric acid, or monocarboxylic acids, such as acetic, propionic, or lactic acid. Further, the inorganic bases suitable for formation of the salts of the esculetin derivative of the present invention are, for example, hydroxides, carbonates or bicarbonates of ammonia, potassium, sodium, lithium, calcium, magnesium, aluminum, or the like. As the the salts with the organic bases, there may be mentioned, for example, mono-, di-, or tri-alkylamine salts, such as methylamine, dimethylamine, or triethylamine, mono-, di-, or tri-hydroxyalkylamine salts, guanidine salts, N-methylglucosamine salts, amino acid salts, or the like.

In the compound of the formula (I) according to the present invention, any one of the groups defined as $R^1$, $R^2$, or $R^3$ may be selected independently of each other, and combined with any one of other groups which are also selected independently. Therefore, the esculetin derivatives of the formula (I) include all the novel compounds composed of any one of all the possible combinations of $R^1$, $R^2$, or $R^3$ selected independently of each other.

The typical examples of the compounds according to the present invention are listed in the following Table 1. In the following Table 1, Me is a methyl group, Et is an ethyl group, $NC_4H_8O$ is a morpholino group, NAcGlc is an N-acetyl glucosamine group, Piv is a 6-pivaloylated group, Glc is a glucose group, Gal is an galactose group, NAcGal is an N-acetyl galactosamine group, and GlcUA is a glucuronic acid group.

TABLE 1

| $R^1$ (or $R^2$) | $R^2$ (or $R^1$) | $R^3$ |
|---|---|---|
| CON(Me)₂ | CON(Me)₂ | H |
| CON(Me)₂ | NAcGlc | H |
| CON(Me)₂ | PivNAcGlc | H |
| CON(Me)₂ | Glc | H |
| CON(Me)₂ | Gal | H |
| CON(Me)₂ | NAcGal | H |
| CON(Me)₂ | GlcUA | H |
| CON(Me)₂ | CON(Me)₂ | 3-Me |
| CON(Me)₂ | NAcGlc | 3-Me |
| CON(Me)₂ | PivNAcGlc | 3-Me |
| CON(Me)₂ | Glc | 3-Me |
| CON(Me)₂ | Gal | 3-Me |

TABLE 1-continued

| $R^1$ (or $R^2$) | $R^2$ (or $R^1$) | $R^3$ |
|---|---|---|
| CON(Me)₂ | NAcGal | 3-Me |
| CON(Me)₂ | GlcUA | 3-Me |
| CON(Me)₂ | CON(Me)₂ | 4-Me |
| CON(Me)₂ | NAcGlc | 4-Me |
| CON(Me)₂ | PivNAcGlc | 4-Me |
| CON(Me)₂ | Glc | 4-Me |
| CON(Me)₂ | Gal | 4-Me |
| CON(Me)₂ | NAcGal | 4-Me |
| CON(Me)₂ | GlcUA | 4-Me |
| CON(Me)₂ | CON(Me)₂ | 3-COOMe |
| CON(Me)₂ | NAcGlc | 3-COOMe |
| CON(Me)₂ | PivNAcGlc | 3-COOMe |
| CON(Me)₂ | Glc | 3-COOMe |
| CON(Me)₂ | Gal | 3-COOMe |
| CON(Me)₂ | NAcGal | 3-COOMe |
| CON(Me)₂ | GlcUA | 3-COOMe |
| CON(Et)₂ | CON(Et)₂ | H |
| CON(Et)₂ | NAcGlc | H |
| CON(Et)₂ | PivNAcGlc | H |
| CON(Et)₂ | Glc | H |
| CON(Et)₂ | Gal | H |
| CON(Et)₂ | NAcGal | H |
| CON(Et)₂ | GlcUA | H |
| CON(Et)₂ | CON(Et)₂ | 3-Me |
| CON(Et)₂ | NAcGlc | 3-Me |
| CON(Et)₂ | PivNAcGlc | 3-Me |
| CON(Et)₂ | Glc | 3-Me |
| CON(Et)₂ | Gal | 3-Me |
| CON(Et)₂ | NAcGal | 3-Me |
| CON(Et)₂ | GlcUA | 3-Me |
| CON(Et)₂ | CON(Et)₂ | 4-Me |
| CON(Et)₂ | NAcGlc | 4-Me |
| CON(Et)₂ | PivNAcGlc | 4-Me |
| CON(Et)₂ | Glc | 4-Me |
| CON(Et)₂ | Gal | 4-Me |
| CON(Et)₂ | NAcGal | 4-Me |
| CON(Et)₂ | GlcUA | 4-Me |
| CON(Et)₂ | CON(Et)₂ | 3-COOMe |
| CON(Et)₂ | NAcGlc | 3-COOMe |
| CON(Et)₂ | PivNAcGlc | 3-COOMe |
| CON(Et)₂ | Glc | 3-COOMe |
| CON(Et)₂ | Gal | 3-COOMe |
| CON(Et)₂ | NAcGal | 3-COOMe |
| CON(Et)₂ | GlcUA | 3-COOMe |
| CONC₄H₈O | CONC₄H₈O | H |
| CONC₄H₈O | NAcGlc | H |
| CONC₄H₈O | PivNAcGlc | H |
| CONC₄H₈O | Glc | H |
| CONC₄H₈O | Gal | H |
| CONC₄H₈O | NAcGal | H |
| CONC₄H₈O | GlcUA | H |
| CONC₄H₈O | CONC₄H₈O | 3-Me |
| CONC₄H₈O | NAcGlc | 3-Me |
| CONC₄H₈O | PivNAcGlc | 3-Me |
| CONC₄H₈O | Glc | 3-Me |
| CONC₄H₈O | Gal | 3-Me |
| CONC₄H₈O | NAcGal | 3-Me |
| CONC₄H₈O | GlcUA | 3-Me |
| CONC₄H₈O | CONC₄H₈O | 4-Me |
| CONC₄H₈O | NAcGlc | 4-Me |
| CONC₄H₈O | PivNAcGlc | 4-Me |
| CONC₄H₈O | Glc | 4-Me |
| CONC₄H₈O | Gal | 4-Me |
| CONC₄H₈O | NAcGal | 4-Me |
| CONC₄H₈O | GlcUA | 4-Me |
| CONC₄H₈O | CONC₄H₈O | 3-COOMe |
| CONC₄H₈O | NAcGlc | 3-COOMe |
| CONC₄H₈O | PivNAcGlc | 3-COOMe |
| CONC₄H₈O | Glc | 3-COOMe |
| CONC₄H₈O | Gal | 3-COOMe |
| CONC₄H₈O | NAcGal | 3-COOMe |
| CONC₄H₈O | GlcUA | 3-COOMe |

The esculetin derivatives of the present invention can be prepared, for example, by the following processes, that is, by reacting a compound of the formula (XI)

(XI)

wherein $R^3$ has the same meaning as above, a compound of the formula (II)

(II)

wherein $R^3$ and $R^6$ have the same meanings as above, or a compound of the formula (II')

(II')

wherein $R^3$ and $R^6$ have the same meanings as above, with a compound of the formula (X)

$$R^5(R^4)NCOX \quad (X)$$

wherein $R^4$ and $R^5$ have the same meanings and X is a halogen atom.

More particularly, the esculetin derivatives of the present invention having two carbamoyl groups [—CON($R^4$)$R^5$] at 6- and 7-positions of the coumarin ring may be prepared by reacting the compound of the formula (XI) with the compound of the formula (X). Further, the esculetin derivatives of the present invention having a monosaccharide or acylated monosaccharide group at 6-position of the coumarin ring and a carbamoyl group at 7-position of the coumarin ring may be prepared by reacting the compound of the formula (II) with the compound of the formula (X). Further, the esculetin derivatives of the present invention having a carbamoyl group at 6-position of the coumarin ring and a monosaccharide or acylated monosaccharide group at 7-position of the coumarin ring may be prepared by reacting the compound of the formula (II') with the compound of the formula (X). Typical examples of the processes for manufacturing the compound having two carbamoyl groups and that for manufacturing the compound having a carbamoyl group will be explained in detail hereinafter, respectively.

(A) The compound having two carbamoyl groups

The reaction scheme (I) is shown as follows:

(XIII)

wherein $R^3$, $R^4$, and $R^5$ have the same meanings as above.

The step 1 in reaction scheme (I) comprises reacting esculetin, or 3- or 4-substituted esculetin derivative (XI) with a halogenated carbamoyl compound (X), preferably a carbamoyl chloride compound, to obtain the esculetin derivative (XIII) of the present invention having carbamoyl groups at 6- and 7-positions.

The carbamoyl chloride compound is commercially available as a common reagent from, for example, Tokyo Kasei Kogyo K. K. The carbamoyl chloride compound in the formula (X) wherein $R^4$ and $R^5$ together with the nitrogen atom attached thereto form a 3- to 7-membered saturated cycloaliphatic amino group may be obtained by reacting a corresponding cyclic amine with phosgene, or the like. The carbamoyl chloride compound of the formula (X) wherein $R^4$ and $R^5$ are the substituents other than said cycloaliphatic amino group may be obtained by reacting a corresponding amine with phosgene, or the like.

Esculetin is commercially available as a reagent from, for example, Tokyo Kasei Kogyo K. K. 4-Methylesculetin is commercially available as a reagent from, for example, Tokyo Kasei Kogyo K. K. Further, 4-substitiuted esculetin compounds can be generally prepared by reacting the compound of the formula (XII):

(XII)

wherein $R^3$ has the same meaning above, with acetic anhydride and sodium acetate in accordance with the Kostanecki-Robinson reaction (T. C. Chadha, H. S. Mahal, J. Chem. Soc., 1933, p. 1495). It is possible to prepare esculetin in the same manner from the compound of the formula (XII) wherein $R^3$ is a hydrogen atom. Further, 4-substituted esculetin compound wherein $R^3$ is a hydroxyl group can be prepared by first forming an esculetin derivative from the compound wherein $R^3$ is a protected hydroxyl group —OB (wherein B is a protecting group), such as a benzyloxy group in the same manner and removing the protecting group from the resulting esculetin derivative by hydrogenolysis. In this case, it is preferable to remove the protecting group after the step 1 is performed in the state that the hydroxy group is protected.

The 3-substituted esculetin compounds can be efficiently prepared from salicylaldehyde in accordance with the Knoevenagel reaction. The 3-substitiuted esculetin compounds can be prepared, for example, in accordance with the reaction:

described in E. C. Horning, J. Amer. Chem. Soc., 69, 968 (1947), or the reaction:

described in D. G. Crosby, J. Org. Chem., 27, 3083 (1962).

The step 1 may be performed in an organic solvent, such as pyridine, triethylamine, diisopropylethylamine, dichloromethane, tetrahydrofuran, N,N-dimethylformamide, or dimethyl sulfoxide, in the presence of a suitable base, such as pyridine or triethylamine, at 10° to 100° C. for 0.1 to 100 hours. The organic solvent is preferably pyridine, because pyridine acts as the base at the same time, and thus it is not necessary to use other base.

(B) The compound having a carbamoyl group

The basic reaction scheme (II) for manufacturing an esculetin derivative of the formula (I) wherein $R^1$ is a carbamoyl group and $R^2$ is a monosaccharide or acylated monosaccharide group, is as follows:

The steps (2) to (13) in the above reaction scheme (II) will be explained hereinafter as steps 2 to 13.

It is noted that the above-mentioned reaction scheme (II) may be applied for the process of manufacturing the esculetin derivative of the formula (I) wherein $R^2$ is a carbamoyl group and $R^1$ is a monosaccharide or acylated monosaccharide group, by replacing the 6-substituent groups of the compounds in the reaction scheme (II) with 7-substituent groups. Therefore, the following explanation as to the reaction scheme (II) includes both processes.

In the reaction scheme (II), first, the compound (IV) having a 7-protected hydroxyl group (or a 6-protected hydroxyl group) is prepared. More particularly, the compound (IV) wherein $R^3$ is a hydrogen atom may be obtained by using, as a starting compound, esculin (that is, an esculetin compound having 6-hydroxy group protected with glucose group, or 7-hydroxyl-6-glucosyloxycoumarin) (IX), or cichoriin (that is, an esculetin compound having 7-hydroxy group protected with glucose group, or 6-hydroxyl-7-glucosyloxycoumarin) and protecting the hydroxyl group of the starting compound with a protecting group (step 2), and then, performing hydrolysis (step 3). Esculin and cichoriin are naturally occurring materials and available as reagents.

Further, it is possible to use esculetin as a starting material and perform a procedure similar to that of step 2 as mentioned below so as to prepare esculetin compound (IV) wherein one of two hydroxyl groups is protected.

When $R^3$ is not a hydrogen atom, the 3- or 4-substituted esculetin compound prepared as above may be used as a starting material to prepare a 3- or 4-substituted esculetin compound (IV) wherein one of two hydroxyl groups is protected, by a reaction similar to that of step 2 described below. For example, it is possible to easily obtain a 3- or 4-substituted esculetin compound having 6- or 7-hydroxyl group protected with a benzyl group, by reacting benzyl chloride therewith in an alcohol solvent in the presence of a basic catalyst such as potassium carbonate. In this case, the compound (IV) having 6- or 7-protected hydroxyl group can be obtained without step 3.

Step 2

This step [(2) in reaction scheme (II)] comprises introducing a protecting group into 7-hydroxyl group of the esculin compound (IX) (wherein Glc is a glucose group) to obtain the compound (VIII). When cichoriin is used as a starting material, a compound having at 6-position a substituent same as that at 7-position of the compound (VIII), and at 7-position a substituent same as that at 6-position of the compound (VIII) can be obtained. In this step, the compound ZX comprising the group Z for protecting the hydroxyl group and the halogen atom X (for example, benzyl chloride or benzyloxycarbonyl chloride) and the compound (IX), for example, esculin or cichoriin, are reacted in an organic solvent in the presence of a base at 4 to 80° C. for 0.5 to 48 hours to obtain the compound (VIII). This reaction is preferably performed in the presence of a chelating agent, for example, 18-crown-6-ether and potassium iodide or without a chelating agent. As the protecting group Z, a group which can be removed by hydrogenolysis, for example, a benzyl or benzyloxycarbonyl group, or the like is preferably used. Examples of the organic solvent are dimethylformamide, methanol, or ethanol, and examples of the base are sodium or potassium carbonate.

Step 3

This step [(3) in reaction scheme (II)] comprises hydrolyzing the esculin compound (VIII) having the 7-protected hydroxyl group to obtain an esculetin compound (IV) having the 7-protected hydroxyl group. Similarly, it is possible to hydrolyze the cichoriin compound having the 6-protected hydroxyl group to obtain an esculetin compound having the 6-protected hydroxyl group. The esculin compound (VIII) having the 7-protected hydroxyl group or cichoriin compound having the 6-protected hydroxyl group is reacted with the mixture of an acid aqueous solution such as a hydrohalogenic acid and an organic solvent such as alcohol at 40° to 120° C., preferably under heating and reflux, for 0.5 to 10 hours to obtain the compound (IV).

Step 4

This step [(4) in reaction scheme (II)] comprises acylating the monosaccharide. For example, the monosaccharide of the formula:

$$R^{61}OH \qquad (VII)$$

wherein OH is 1-hydroxyl group, and $R^{61}$ is a monosaccharide group having at least one further free hydroxyl group in addition to the 1-hydroxyl group, and acid anhydride of the formula:

$$A_2O$$

wherein A is an acyl group, or acyl halide of the formula:

$$AX$$

wherein A is an acyl group and X is a halogen atom, may be reacted in the presence of a base, such as pyridine or sodium hydroxide, and, if necessary, in a suitable solvent, for example, chloroform, methanol, water, or the like, to obtain the acylated monosaccharide of the formula:

$$R^{62}OA \qquad (VI)$$

wherein $R^{62}$ is a monosaccharide group having at least one acylated hydroxy group which was the free hydroxyl group in addition to the 1-hydroxyl group in $R^{61}$, and A has the same meaning as above. The reaction temperature is generally $-20°$ C. to $+50°$ C., preferably room temperature. The reaction is generally carried out for 1 hour to 2 days.

Step 5

This step [(5) in reaction scheme (II)] comprises substituting a halogen atom for the 1-acyloxyl group of the acylated monosaccharide (VI). For example, gaseous hydrogen halide of the formula

HX wherein X is a halogen atom, dissolved in carboxylic anhydride compound of the formula $A_2O$ wherein A is an acyl group, such as acetic anhydride, may be reacted with the acylated monosaccharide compound of the formula $$R^{62}OA \quad (VI)$$

to obtain the acylated monosaccharide compound of the formula $$R^{62}X \quad (V)$$

having a halogen atom at 1-position with which the 1-acyloxyl group was substituted. The reaction temperature is generally $-20°$ C. to $+50°$ C., preferably room temperature. The reaction is generally carried out for 0.1 hour to 10 days.

Step 6

This step [(6) in reaction scheme (II)] comprises obtaining the above-mentioned compound $R^{62}X$ (V) by one step reaction from the above-mentioned monosaccharide compound $R^{61}OH$ (VII). For example, an acyl halide (AX) may be reacted with the monosaccharide compound $R^{61}OH$ (VII) to obtain the compound $R^{62}X$ (V). The reaction temperature is generally $4°$ C. to $80°$ C. The reaction is generally carried out for 0.5 hours to 2 days.

In the above steps 2, 4, 5, and 6, the halogen atoms X indicated by may be different from each other.

Step 7

This step [(7) in reaction scheme (II)] comprises introducing the acylated monosaccharide group $R^{62}$ to the 6-(or 7-) free hydroxyl group in the esculetin compound (IV) having the 7-(or 6-) protected hydroxyl group. For example, the compound (IV) may be reacted with the monosaccharide derivative (V) in an organic solvent containing alkali aqueous solution, such as an aqueous caustic alkali solution/acetone solution at $4°$ to $80°$ C. to obtain the compound (IIIa). Alternatively, it is possible to obtain the compound (IIIa) by dissolving the compound (IV) and monosaccharide derivative (V) in an organic solvent such as chloroform or acetonitrile, then adding dropwise a solution of an ammonium halide salt having an organic group (phase transfer catalyst) or triethylamine or the like (basic catalyst) dissolved in an aqueous alkali solution to the above solution at $4°$ to $50°$ C., and performing a reaction at $4°$ to $80°$ C. for 0.5 hours to 10 days. An example of the aqueous alkali solution is aqueous sodium hydroxide solution, and an example of the ammonium halide salt having an organic group is benzyltriethylammonium chloride. The phase transfer catalyst means a catalyst which can freely move from an aqueous phase to an organic phase, and vice versa.

Step 8

This step [(8) in reaction scheme (II)] comprises hydrogenolyzing the compound (IIIa) having the acylated monosaccharide group $R^{62}$ and the group Z for protecting a hydroxyl group to obtain a compound (IIa) having the acylated monosaccharide group $R^{62}$. The hydrogenolysis may be performed by a reaction with hydrogen gas in the presence of a palladium or platinum catalyst at $4°$ to $80°$ C. for 0.5 to 48 hours. The palladium catalyst which may be used is preferably palladium-barium sulfate, palladium-carbon, or the like.

Step 9

This step [(9) in reaction scheme (II)] comprises deacylating the compound (IIIa) having an acylated monosaccharide group $R^{62}$ and the group Z for protecting a hydroxyl group to obtain a compound (IIIb) having a monosaccharide group $R^{61}$ and the group z for protecting a hydroxyl group. The deacylation may be carried out, for example, by dissolving the compound (IIIa) in an organic solvent such as methanol and then performing a reaction with an alkali metal, such as potassium or sodium, dissolved in alcohol such as methanol while passing a stream of inert gas (for example, nitrogen or argon gas). The reaction temperature is generally $4°$ to $70°$ C. and the reaction is generally carried out for 0.1 to 72 hours.

Step 10

This step [(10) in reaction scheme (II)] comprises hydrogenolyzing the compound (IIIb) having the monosaccharide group $R^{61}$ and the group Z for protecting a hydroxyl group to obtain the compound (IIb) having the monosaccharide $R^{61}$. The hydrogenolysis is performed by a reaction with hydrogen gas in the presence of a palladium or platinum catalyst at $4°$ to $70°$ C. for 0.1 to 48 hours. The palladium catalyst which may be used is preferably palladium-barium sulfate, palladium-carbon, or the like.

Step 10' (pretreatment of Step 10)

If step 10 is performed after converting (other than acylating) the monosaccharide group $R^{61}$ of the compound (IIIb) to another monosaccharide group $R^{61}$, it is possible to obtain a corresponding compound (IIb) having another monosaccharide group $R^{61}$. For example, when the monosaccharide group $R^{61}$ has —$CH_2OH$, it is possible to obtain a compound (IIb) having another monosaccharide group $R^{61}$ containing —COOH after oxidizing the group —$CH_2OH$ to —COOH. For example, it is possible to convert the glucose group(s) to glucuronic acid group(s) by oxidization.

If step 10 is performed after acylating the hydroxyl group in the monosaccharide group $R^{61}$, for example, pivaloylating the 6-hydroxy group in a hexose group $R^{61}$, of the compound (IIIb) to convert the acylated monosaccharide group $R^{62}$ carried on the compound (IIIa) to another $R^{62}$, it is possible to obtain a compound (IIb) having the acylated monosaccharide group different from that on the compound (IIIa). The acylation of the hydroxyl group in the monosaccharide group $R^{61}$ can basically be performed in the similar manner as in step 4.

Step 11

This step [(11) in reaction scheme (II)] comprises deacylating the compound (IIa) having an acylated monosaccharide group $R^{62}$ to obtain a compound (IIb) having a monosaccharide group $R^{61}$. The deacylation can basically be performed in the same manner as in step 9.

Step 12

This step [(12) of the reaction scheme (II)] comprises reacting the compound (IIa) having the acylated monosaccharide group $R^{62}$ with a halogenated carbamoyl compound (X) to obtain an esculetin derivative (Ia) having a carbamoyl group and an acylated monosaccharide group $R^{62}$. The reaction may be performed in an organic solvent, such as pyridine, triethylamine, diisopropylethylamine, dichloromethane, tetrahydrofuran, N,N-dimethylformamide, or dimethyl sulfoxide in the presence of a suitable base, such as pyridine, triethylamine, or aniline, at 10° to 100° C. for 0.1 to 100 hours. It is preferable to use pyridine as the organic solvent, because pyridine acts as the base at the same time, and thus it is not necessary to use other base.

Step 13

This step [(13) in reaction scheme (II)] comprises reacting the compound (IIb) having the monosaccharide group $R^{61}$ prepared in step 10 [or having acylated monosaccharide group $R^{62}$ diffrent from the group $R^{62}$ carried on the compound (IIIa)] with a halogenated carbamoyl compound (X) to obtain an esculetin derivative (Ib) having a carbamoyl group and the above various acylated monosaccharide group $R^{61}$. The reaction in step (13) can basically be performed in the same manner as in step 12.

The esculetin derivative wherein the monosaccharide group $R^{61}$ or $R^{62}$ has an N-acylamino group may be deacylated to obtain the esculetin derivative having a carbamoyl group and an amino sugar group $R^{61}$ without an acyl group. The deacylation may be performed by reacting the esculetin derivative wherein the monosaccharide group is an N-acylamino sugar group with an aqueous alkali solution, preferably 0.1N to 12N NaOH, at 40° to 120° C. for 1 to 48 hours.

The free esculetin derivative of the present invention may be converted to the corresponding salt, a salt may be converted into other salt, and the salt of the esculetin derivative of the present invention may be converted to the free esculetin derivative, by the processes known per se. For example, a salt may be formed from the esculetin derivative having an N-acetyl glucosamine or uronic acid group containing a free carboxylic acid group. More particularly, a free carboxylic acid group can be converted to an alkaline salt by reacting the above esculetin derivative with equimolar alkali hydroxide, such as sodium or potassium hydroxide. Further, the salt can be converted to a free compound by acidifying an aqueous solution thereof with hydrochloric or sulfuric acid. The compound having a free amino group may be reacted with an equivalent amount of an organic acid, such as malic, citric or acetic acid to form the corresponding salt. An inorganic acid, such as hydrochloric or sulfuric acid may be used to form hydrochloride or sulfate. The inorganic salt can be converted to a free base by treatment with an alkali. The salt is water soluble, whereas the free compound is hardly soluble in water, and thus can be isolated by precipitation.

The reaction product can be purified by extraction, chromatography, recrystallization, or reprecipitation. The structure of the purified product may be confirmed by, for example, the infrared absorption spectrum, ultraviolet absorption spectrum, nuclear magnetic resonance absorption spectrum, elemental analysis, or mass spectrum.

The toxicity of the esculetin derivatives of the present invention was examined. Typical examples of the present derivatives were administered orally at a dose of 2000 mg/kg (body weight) to male mice and male rats which were then observed for seven days. No deaths and no remarkable toxicity were observed. The esculetin derivatives of the present invention are extremely safe compounds (see Example 13).

The esculetin derivative of the present invention is taken up and retained in the femoral head cartilages (FHC) in a higher concentration for a longer time as compared to esculetin in mouse FHC models (see Example 15).

The esculetin derivative of the present invention exhibits, as a pharmacological effect, the function to inhibit production of matrix metalloproteinases (see Example 14).

Accordingly, the esculetin derivatives of the present invention or pharmaceutically acceptable salts thereof are useful as effective ingredients of matrix metalloproteinase inhibitors for treating various types of diseases accompanying the matrix decomposition, by virtue of the function to inhibit production of matrix metalloproteinases. Examples of such various types of diseases accompanying the matrix decomposition are arthropathy, such as rheumatoid arthritis, osteoarthritis, periarthritis humeroscapularis, shoulder-arm-neck syndrome, lumbago, or the like, corneal ulcer, wound, granuloma, periodontosis, vesicular exanthem, glomerular nephritis, pulmonary emphysema, bone resorption, infiltration and metastasis of cancer, or the like.

The pharmaceutical composition containing as an effective ingredient the esculetin derivative of the present invention or pharmaceutically acceptable salts thereof, particularly the matrix metalloproteinase inhibitors, may be in the form of any conventional formulation. The pharmaceutical composition may contain the derivative alone, or a mixture of the derivative with any pharmaceutically acceptable carrier or diluent. The amount of the effective ingredient contained in the composition is not particularly limited, but may for example be 0.01 to 100% by weight, preferably 0.1 to 70% by weight.

The pharmaceutical composition, in particular the matrix metalloproteinase inhibitor, of the present invention may be administered orally or parenterally.

The dose of the pharmaceutical composition, in particular the matrix metalloproteinase inhibitor, of the present invention varies with the patient (mammal, particularly human), age, individual differences, symptom, and the like. Generally speaking, however, when a human is treated, the dose of oral administration of the esculetin derivative of the present invention is in the range of 0.1 to 500 mg/kg (body weight) per day, preferably 0.5 to 200 mg/kg (body weight), which is usually divided into 1 to 4 dosages in a day, although the dose outside the above range may sometimes be administered.

The esculetin derivatives of the present invention are useful for treating various types of diseases relating to the matrix metalloproteinase, because of the function to inhibit production of matrix metalloproteinases.

There are various types of arthropathy, for example, rheumatoid arthritis, rheumatic fever, and osteoarthritis. Although there are considerable differences of the causes and conditions between rheumatoid arthritis and osteoarthritis, the articular function becomes eventually obstructed by the destruction of the cartilage in both of rheumatoid arthritis and osteoarthritis. Accordingly, if the destruction of the cartilage or the tissue may be depressed, symptoms will be improved.

The articular cartilage is composed of chondrocytes and the cartilage matrix. The cartilage matrix has a three-dimensional structure which is formed by non-covalently binding the type II collagen (the fibrous protein produced by the chondrocytes) and the proteoglycan (glycoprotein complex), with hyaluronic acid whereby they are complicatedly entangled. The matrix holds a large amount of water, which enables the normal articular functions to be maintained. The main polysaccharide constituting the proteoglycan is glycosaminoglycan, which is composed of chondroitin sulfate and keratan sulfate. It is known that matrix proteinases, such as collagenase, gelatinase, stromelysin, or matrilysin, are activated and the destruction of the matrix are increased in rheumatoid arthritis, osteoarthritis, or the like. Accordingly, the matrix metalloproteinase inhibitors would be effective in the treatment of the diseases.

Metastatic cancer cells have not only the basic abilities of tumor cells, such as abnormal proliferation potency and inducibility of vascularization, or evasion from immune response, but also the abilities for abnormal motility and adhesion properties, production of extracellular matrix proteinases, proliferation in infiltration and metastasis location, vascularization, and the like. It has become clear that extracellular proteinases positively take part in processes of infiltration, proliferation, vascularization, and the like. Therefore, a compound which may suppress production, secretion, or activation of the extracellular matrix proteinase would be useful for prevention of cancer metastasis.

The esculetin derivative of the present invention has carbamoyl and/or substituted carbamoyl groups on both of 6and 7-hydroxy group of the esculetin compound, or has a carbamoyl or substituted carbamoyl group on one of 6- and 7-hydroxy group of the esculetin compound and a monosaccharide group having the structure similar to that of the cartilage matrix components at the other of 6- and 7-hydroxy group. Therefore, the esculetin derivative of the present invention may be a matrix metalloproteinase inhibitor having high efficiency for the utilization in the body.

EXAMPLES

The present invention now will be further illustrated by, but is by no means limited to, the following Examples.

Example 1

Preparation of 6,7-bis(N,N-dimethylcarbamoyloxy) coumarin [I-1] (Step 1)

Esculetin (Tokyo Kasei Kogyo K. K.) [XI-1] (300 mg) was dissolved in pyridine (12 ml). N,N-Dimethylcarbamoyl chloride (0.62 ml) was added to the solution and the mixture was heated to 60° C. The mixture was reacted at the same temperature for 4 hours, and then, a saturated ammonium chloride aqueous solution (50 ml) was added. The mixture was extracted with chloroform (50 ml) three times. The organic layers were dried over sodium sulfate, and concentrated under reduced pressure. The residue was purified by silica gel column chromatography [Kieselgel (50 g), chloroform/methanol (10:1)] to obtain the above-captioned compound (536.1 mg, yield=99.4%) as a white solid.

Melting point: 160°–161° C. Mass spectrum (m/e, EI): 320 (M$^+$) $^1$H-NMR (DMSO-d6, 500MHz, δ ppm): 3.02 and 3.08 (2s, 6H, CONMe$_2$), 6.39 (d, 1H, H-4), 7.26 and 7.38 (2s, 2H, H-5, H-8), 7.63 (d, 1H, H-3) IR spectrum (KBr-disk, ν cm$^{-1}$): 1725s, 1390m, 1160s, 1150s, 1130s Example 2

Preparation of 7-benzyloxy-6-hydroxycoumarin [IV-2] (Steps 2 and 3)

Esculin (1.0 g), benzyl chloride (1.0 g), potassium carbonate (0.7 g), catalytic amounts of 18-crown-6-ether and potassium iodide, and dimethylformamide (40 ml) were placed in an eggplant-shaped flask (100 ml). The mixture was reacted while stirred at 60° C. for 8 hours. The reaction mixture was concentrated under reduced pressure and the residue was poured into ice water. The precipitated crystals were filtered out and recrystallized from methanol to obtain 7-benzyloxy-6-D-glucopyranosyloxycoumarin (VIII-2) (melting point=184° to 186° C., mass spectrum (M$^+$)=430, yield=86.4%).

The compound [VIII-2] (0.6 g) was heated under reflux for 1 hour in a mixture of methanol (35 ml) and 10% hydrochloric acid (35 ml). The reaction mixture was concentrated under reduced pressure. The crystals were filtered out, and the above-captioned compound [IV-2] (yield= 90.3%) was obtained.

Melting point: 193°–195° C. Mass spectrum (M$^+$): 268

Example 3

Preparation of 2-acetamido-1,3,4,6-tetra-O-acetyl-2-deoxy-α-D-glucopyranose [VI-2] (step 4 wherein a sugar component is glucosamine)

A solution of a mixture of acetic anhydride (12.25 g) and dry pyridine (18.98 g) was placed in an eggplant-shaped flask (500 ml), and then N-acetyl-D-glucosamine [VII-2] (4.43 g) was added at room temperature portionwise. The resulting solution was stirred at room temperature overnight. The reaction solution was poured onto ice water (150 ml), and then, extracted with ether (100 ml) twice. The aqueous layers were concentrated under reduced pressure at 65° C. to obtain the crude product (9.407 g). The crude product was dissolved in ethyl acetate (150 ml). The resulting solution was washed with water (5 ml), dried over sodium sulfate, and further dried under reduced pressure by a rotary evaporator to obtain an oily product. Ether was added to the oily product and the substance was triturated to obtain the above-captioned compound (6.47 g, yield=83.1%) as white crystals.

Rf: 0.39 (ethyl acetate) Melting point: 185°–187° C. $^1$H-NMR (CDCl$_3$, δ ppm): 1.94 (s, 3H), 2.04 (s, 3H), 2.06 (s, 3H), 2.09 (s, 3H), 2.20 (s, 3H), 4.00 (m, 1H, C5-H), 4.07 (d, 1H, C6-H), 4.25 (dd, 1H, C6-H), 4.48 (dt, 1H, C2-H), 5.23 (m, 2H, C3, 4-H), 5.72 (d, 1H, NH), 6.17 (d, 1H, C1-H) IR spectrum (KBr, ν cm$^{-1}$): 3360s, 3025m, 2980m, 1740s, 1675s, 1520s, 1425s, 1380s, 1230s, 1130s, 1025s, 940s, 890m, 840m Example 4

Preparation of 2-acetamido-3,4,6-tri-O-acetyl-1-chloro-2-deoxy-α-D-glucopyranose [V-2] (step 5 wherein a sugar component is glucosamine)

Acetic anhydride (6 ml) was added to an eggplant-shaped flask (50 ml). Dry hydrogen chloride gas was blown into the acetic anhydride up to a saturated state. There was an approximately 1.5 g increase in weight. To the solution, 2-acetamido-1,3,4,6-tetra-O-acetyl-2-deoxy-α-D-glucopyranose [VI-2] prepared in Example 3 (2.0 g) was added and the mixture was stirred at room temperature for 6 days. Methylene chloride (25 ml) was added to the reaction mixture and the reaction mixture was washed with a saturated sodium hydrogencarbonate aqueous solution (20 ml) twice. The collected organic layers were dried over anhydrous sodium sulfate, and concentrated to obtain a crude product (1.32 g). The crude product was purified by silica gel chromatography [diameter=2.5 cm, length=10.5 cm, silica gel=15 g, n-hexane/ethyl acetate (1:4)] to obtain the above-captioned compound (871.7 mg, yield=46.4%) as white crystals.

Rf: 0.67 (ethyl acetate) Melting point: 125°–126° C. Mass spectrum (m/e): 731 (2M+1), 356 (100), 324, 306, 228, 168, 150 $^1$H-NMR (CDCl$_3$, δ ppm): 1.99 (s, 3H), 2.06 (s, 6H), 2.11 (s, 3H), 4.14 (d, 1H, C5-H), 4.28 (m, 2H, C6-H), 4.54 (dt, 1H, C2), 5.22 (t, 1H, C4-H), 5.33 (t, 1H, C3-H), 5.98 (d, 1H), 6.19 (d, 1H, C1-H) IR spectrum (KBr, ν cm$^{-1}$): 3300w, 1750s, 1650m, 1550m, 1440m, 1380m, 1295m, 1235s, 1215s, 1120m, 1035m, 980w, 918w, 895w

Example 5

Preparation of 2-acetamido-3,4,6-tri-O-acetyl-1-chloro-2-deoxy-α-D-glucopyranose [V-2] (step 6 wherein a sugar component is glucosamine)

Acetyl chloride (25 ml) was poured in an eggplant-shaped flask (200 ml) and then N-acetyl-D-glucosamine (VII-2) (12.5 g) was added portionwise under stirring. After 4 hours, the reaction solution generated heat and a gentle reflux occurred. The reaction solution was stirred overnight, whereupon a light red viscous solid was obtained. The solid was dissolved by adding methylene chloride (100 ml). The solution was neutralized with a cold saturated sodium hydrogencarbonate aqueous solution. The collected organic layers were washed with distilled water, dried over anhydrous sodium sulfate, and then concentrated to obtain a crude product (23.8 g). The crude product was crystallized from ether to obtain the above-captioned compound (16.0 g, yield=77%) as white crystals.

Example 6

Preparation of 6-(β-2-acetamido-3,4,6-tri-O-acetyl-2-deoxy-D-glucopyranosyloxy)-7-benzyloxycoumarin [IIIa-2] (step 7 wherein a sugar component is glucosamine)

To an eggplant-shaped flask (25 ml), 2-acetamido-3,4,6-tri-O-acetyl-1-chloro-2-deoxy-α-D-glucopyranose [V-2] (914.5 mg) prepared in Example 4 or 5, 7-benzyloxy-6-hydroxycoumarin [IV-2] (335.5 mg) prepared in Example 2, and chloroform (10 ml) were added to produce a suspension. Benzyltriethylammonium chloride (113.9 mg) dissolved in 1.25N NaOH (12.5 ml) was added to the suspension. The suspension was refluxed in an argon atmosphere for 3 hours, and then allowed to be cooled to room temperature. The reaction mixture was diluted with methylene chloride (40 ml), and the organic layer was separated. The aqueous layer was extracted with methylene chloride (20 ml). The collected organic layers were washed with saturated saline (10 ml), dried over anhydrous sodium sulfate, and concentrated to obtain a crude product (1.16 g). The crude product was treated with methanol/methylene chloride to obtain the above-captioned compound (150.4 mg, yield=21.1%) as white needle crystals.

Rf: 0.56 (ethyl acetate) Melting point: 224°–227° C. Mass spectrum (m/e): 597, 537, 523,419, 329, 268, 209, 167, 125 (100) $^1$H-NMR (CDCl$_3$, δ ppm): 1.54 (s, 3H), 2.02 (s, 3H), 2.03 (s, 3H), 2.04 (s, 3H), 3.07 (m, 1H, C5-H), 4.14 (m, 2H, C-6, C2-H), 4.26 (dd, 1H, C6-H), 5.04 (d, 1H, C1-H), 5.13 (s, 2H, benzyl), 5.11 (q, 1H, C4-H), 5.23 (t, 1H, C3-H), 6.29 (d, C3), 6.92 (s, 1H), 7.26 (s, 1H), 7.46 (m, 5H), 7.59 (d, C4) IR spectrum (KBr, ν cm$^{-1}$): 3300m, 2975w, 2900w, 1740s, 1660s, 1620s, 1555m, 1520m, 1440m, 1380s, 1230s, 1180m, 1140m, 1120m, 1060s, 1040s, 930m, 900m, 870m, 810s, 730m

Example 7

Preparation of 6-(β-2-acetamido-2-deoxy-D-glucopyranosyloxy)-7-benzyloxycoumarin [IIIb-2] (Step 9 wherein a sugar component is glucosamine)

In an eggplant-shaped flask (100 ml), 6-(β-2-acetamido-3,4,6-tri-O-acetyl-2-deoxy-D-glucopyranosyloxy)-7-benzyloxycoumarin [IIIa-2] (351 mg) prepared in Example 6 and methanol (90 ml) were placed to produce a suspension. Five drops of a methanol solution of sodium methoxide (28%) were added to the suspension. The suspension was heated to 40° C. and stirred. The reaction mixture became transparent after 10 minutes and a white precipitate was formed after 20 minutes. The reaction solution was stirred at room temperature for 1.5 hours, and then neutralized with 0.1N HCl. The precipitate was collected by filtration through a glass filter, washed with methanol, and dried under reduced pressure to obtain the above-captioned compound (262.6 mg, yield=95.1%) as white needle crystals.

Melting point: 244°–246° C. Rf: 0.73 (chloroform/methanol/water (7:3:0.5)) Mass spectrum (m/e): 472 (M+1), 382, 269, 253, 204, 185, 168, 138, 91 $^1$H-NMR (DMSO-d6, δ ppm): 1.73 (s, 3H, N-Ac), 3.23 (q, 1H), 3.43 (t, 1H), 3.51 (m, 1H), 3.73 (q, 2H), 5.02 (d, 1H), 5.25 (s, 2H, benzyl), 6.30 (d, 1H, coumarin), 7.12 (s, 1H, coumarin), 7.31 (t, 1H, para-benzyl), 7.39 (t, 2H, meta-benzyl), 7.43 (s, 1H, coumarin), 7.48 (d, 2H), 7.79 (d, 1H, AcNH), 7.89 (d, 1H, coumarin) IR spectrum (KBr, ν cm$^{-1}$): 3405s, 3275m, 2900w, 1750s, 1665s, 1615m, 1540m, 1430m, 1390m, 1380m, 1310s, 1270s, 1240w, 1175m, 1110m, 1090s

Example 8

Preparation of 6-(β-2-acetamido-2-deoxy-D-glucopyranosyloxy)-7-hydroxycoumarin [IIb-2] (step 10 wherein sugar component is glucosamine)

In an eggplant-shaped flask (100 ml), 6-(β-2-acetamido-2-deoxy-D-glucopyranosyloxy)-7-benzyloxycoumarin [IIIb-2] (315.5 mg) prepared in Example 7 and 15% water-containing dimethoxyethane (60 ml) were placed to produce a solution. To the solution, 10% palladium-carbon (hereinafter referred to as Pd/C) (24 mg) was added as a catalyst and the mixture was stirred in a hydrogen atmosphere at room temperature for 1 hour. The solvent was removed from the reaction mixture under reduced pressure to obtain gray powder. To the resulting powder, a mixture (435 ml) of water/tetrahydrofuran/methanol (5:1:0.2) was added. The powder was dissolved by heating to 75° C. The catalyst was filtered out. The filtrate was concentrated to 50 ml and allowed to stand overnight in a refrigerator to obtain the above-captioned compound (228.0 mg, yield=89.3%) as white needle crystals.

Rf: 0.56 [chloroform/methanol/water (7:3:0.5)] Melting point: 265°–266° C.

Elemental analysis for $C_{17}H_{19}O_9N$ Found: C 53.25, H 4.91, N 3.55 Calculated: C 53.55, H 5.02, N 3.67 $^1$H-NMR (CDCl$_3$, δ ppm): 1.83 (s, 3H), 3.23 (t, 1H, C3-H), 3.35 (m, 1H), 3.48 (t, 1H), 3.52 (m, 1H), 5.00 (d, 1H, C1-H), 6.24 (d, 1H, coumarin), 6.83 (s, 1H, coumarin), 7.36 (s, 1H, coumarin), 7.88 (d, 1H) IR spectrum (KBr, ν cm$^{-1}$): 3375s, 3240w, 2930w, 1640s, 1665s, 1600s, 1550m, 1405m, 1275m, 1255m, 1225w, 1172w, 1140w, 1120m, 1085m, 1042m, 1025w, 995m, 930m, 890m, 861m, 820m

Example 9

Preparation of 6-(β-2-acetamido-2-deoxy-D-glucopyranosyloxy)-7m(N,N-dimethylcarbamoyloxy)coumarin [Ib-2] (Step 13 wherein a sugar component is glucosamine)

In pyridine (365 ml), 6-(β-2-acetamido-2-deoxy-D-glucopyranosyloxy)-7-hydroxycoumarin [IIb-2] (7.30 g) prepared in Example 8 was suspended. N,N-

Dimethylcarbamoyl chloride (1.85 ml) was added to the suspension and the mixture was stirred at 60° C. for a day. The reaction mixture was concentrated under reduced pressure. Ethanol was added to the residue and the mixture was heated. Pyridine hydrochloride was removed by filtration on heating. The filtrate was recrystallized from ethanol to obtain the above-captioned compound (4.80 g, yield= 55.4%) as a white solid.

Melting point: 148.0°–149.0° C. Mass spectrum (EI, m/e): 453 (M+1) $^1$H-NMR (DMSO-d6, 500MHz, δ ppm): 1.79 (s, 3H, Ac), 2.90 and 3.01 (2s, 6H, Me$_2$NCO), 3.22–3.28 (m, H-4'), 3.34–3.41 (m, 2H, H-3', H-5'), 3.50–3.56 (m, 1H, H-6b'), 3.70–3.79 (m, 2H, H-2', H-6a'), 4.59 (t, 1H, 6'-OH), 4.98 (d, 1H, H-1'), 5.05 (d, 1H, 3'-OH), 5.12 (d, 1H, 4'-OH), 6.46 (d, 1H, H-4'), 7.25 and 7.44 (2s, 2H, Ar), 7.69 (d, 1H, NHAc), 7.98 (d, 1H, H-3) IR spectrum (KBr-disk, ν cm$^{-1}$): 3550s, 3450s, 1745s, 1725s, 1170m, 1100m Example 10

Preparation of 6-(β-2-acetamido-2-deoxy-6-O-pivaloyl-D-glucopyranosyloxy)-7-benzyloxycoumarin [IIIb-2p] [step 10 wherein a sugar component is glucosamine (introduction of one acyl group)]

In anhydrous pyridine (200 ml), 6-(β-2-acetamido-2-deoxy-D-glucopyranosyloxy)-7-benzyloxycoumarin [IIIb-2] (10.0 g) prepared in Example 7 was suspended. To the suspension, pivalic anhydride (4.74 g) and 4-dimethylaminopyridine (2.59 g) were added, and the mixture was stirred at room temperature for 3 days. After the reaction was completed, the solvent was evaporated under reduced pressure. The residue was purified by silica gel column chromatography [Kieselgel 60 (500 g), chloroform/methanol (15:1)] to obtain the above-captioned compound (9.11 g, yield=77%) as a white solid.

Melting point: 179.5°–182.0° C. Mass spectrum (m/e, FAB): 556 (M+1) $^1$H-NMR (CDCl$_3$, 500MHz, δ ppm): 1.06 (s, 9H, tBu), 1.76 (s, 3H, CH$_3$CO—), 3.24 (td, 1H, H-4'), 3.48 (br q, 1H, H-3'), 3.57–3.61 (m, 1H, H-5'), 3.72 (q, 1H, H-2'), 4.05 (dd, 1H, H-6'a), 4.36 (d, 1H, H-6'b), 5.12 (d, 1H, H-1'), 5.18 (d, 1H, 3'—OH), 5.24 (d, 1H, PhCH$_2$—), 5.27 (d, 1H, PhCH$_2$—), 5.38 (d, 1H, 4'—OH), 6.31 (d, 1H, H-4), 7.18 (s, 1H, H-5) IR spectrum (KBr disk, ν cm$^{-1}$): 3400m, 1725s, 1655m, 1615m, 1275s Example 11

Preparation of 6-(β-2-acetamido-2-deoxy-6-O-pivaloyl-D-glucopyranosyloxy)-7-hydroxycoumarin [IIb-2P] (step similar to step 10 wherein a sugar component is glucosamine)

10% Pd/C. (30 mg) was added to a solution of 6-(β-2-acetamido-2-deoxy-6-O-pivaloyl-D-glucopyranosyloxy)-7-benzyloxycoumarin [IIIb-2P] (532 mg) prepared in Example 10 in dimethoxyethane (16 ml). The mixture was stirred in a hydrogen atmosphere at room temperature for 3 hours. After the reaction was completed, the catalyst was removed by filtration. The solvent was evaporated under reduced pressure to obtain a light yellow solid (443 mg). The solid was recrystallized from hot water to obtain the above-captioned compound (358 mg, yield=77%) as white needle crystals.

Melting point: 133.0°–136.0° C. Mass spectrum (m/e, FAB): 466 (M+1) $^1$H-NMR (DMSO-d6, 500MHz, δ ppm): 1.06 (s, 9H, tBu), 1.84 (s, 3H, CH$_3$CO—), 3.23 (td, 1H, H-4'), 3.53 (br q, 1H, H-3'), 3.57–3.61 (m, 1H, H-5'), 3.62 (q, 1H, H-2'), 4.04 (dd, 1H, H-6'a), 4.39 (d, 1H, H-6'b), 5.07 (d, 1H, H-1'), 5.19 (d, 1H, 3'—OH), 5.38 (d, 1H, 4'—OH), 6.24 (d, 1H, H-4), 6.81 (s, 1H, H-5), 7.28 (s, 1H, H-8), 7.90 (d, 1H, H-3), 7.94 (d, 1H, —NHCOCH$_3$), 9.91 (br s, 1H, ArOH) IR spectrum (KBr disk, ν cm$^{-1}$): 3400s, 1720s, 1650s, 1620s, 1565s, 1300s, 1280s, 1255s, 1170m, 1140m, 1070s Example 12

Preparation of 6-(β-2-acetamido-2-deoxy-6-O-pivaloyl-D-glucopyranosyloxy)-7-(N,N-carbamoyloxy)coumarin [Ib-2P] (step similar to step 13 wherein a sugar component is glucosamine)

In pyridine (25 ml), 6-(β-2-acetamido-2-deoxy-6-O-pivaloyl-D-glucopyranosyloxy)-7-hydroxycoumarin [IIb-2P] (618 mg) prepared in Example 11 was dissolved. N,N-Dimethylcarbamoyl chloride (146 mg) was added to the solution and the reaction was carried out at 70° C. for 5.5 hours. The reaction mixture was concentrated under reduced pressure to obtain the residue (solid). The solid was recrystallized from water to obtain the above-captioned compound (370 mg, yield=52%) as white crystals.

Rf: 0.39 [chloroform/methanol (10:2)] Melting point: 244°–245° C. (decomposition) Mass spectrum (m/e, FAB): 537 (M+1) $^1$H-NMR (DMSO-d6, 500MHz, δ ppm): 1.11 (s, 9H, (CH$_3$)$_3$C—), 1.80 (s, 3H, CH$_3$CO—), 2.90 (s, 3H, (CH$_3$)$_2$N—), 3.02 (s, 3H, (CH$_3$)$_2$N—), 3.23 (m, 1H, H-4'), 3.40 (m, 1H, H-3'), 3.72 (m, 1H, H-5'), 3.76 (m, 1H, H-2'), 4.03 (dd, 1H, H-6'a), 4.39 (d, 1H, H-6'b), 5.07 (d, 1H, H-1'), 5.17 (d, 1H, 3—OH), 5.41 (d, 1H, 4—OH), 6.48 (d, 1H, H-4), 7.26 (s, 1H, H-5), 7.44 (s, 1H, H-8), 7.73 (d, 1H, —CONH—), 7.92 (d, 1H, H-3) IR spectrum (KBr-disk, ν cm$^{-1}$): 3375s, 2970w, 2915w, 2875w, 1740s, 1720s, 1655m, 1545m, 1430m, 1380m, 1285s, 1260m, 1170s, 1140m, 1090m, 1050m Example 13

Acute Toxicity of Esculetin Derivatives

The acute toxicity of the esculetin derivatives of the present invention was examined using Crj: CD-1 (ICR) male mice (6 weeks old) and Wistar male rats (6 weeks old). After 6-(β-2-acetamido-2-deoxy-D-glucopyranosyloxy)-7-(N,N-dimethylcarbamoyloxy)coumarin [Ib-2] (Example 9) was administered orally at doses of 1000 and 2000 mg/kg, the conditions of animals were observed for 7 days. No deaths were observed. Further, no change was observed in comparison with the control group in each of the general state and body weight. Similar results are observed for other compound, that is, 6-(β-2-acetamido-2-deoxy-6-O-pivaloyl-D-glucopyranosyloxy)-7-(N,N-carbamoyloxy)coumarin [Ib-2P]. In the experiments as above, two animals were used for each group.

Example 14

Function to Inhibit Production of Interstitial Collagenase (MMP-1) in Rabbit Cartilage Organ Culture System After the articular cartilages were collected from the shoulder and knee of rabbits (New Zealand White Rabbits, male, 6 weeks old) and divided into small pieces, cultivation experiment was started using Dulbecco's MEM medium containing 0.2% lactoalbumin. The compounds to be tested were dissolved in dimethylsulfoxide (DMSO) and then added to the medium. The concentration of DMSO was 0.25% by volume to the medium. After 2 hours from addition of the compounds to be tested, 100 units/ml of interleukin-1α (hereinafter referred to as the IL-1α) was added as a stimulant, and the cultivation was performed for 48 hours. Thereafter, the activity of MMP-1 in the supernatant of the culture was measured. Collageno kit (CLN-100) (Cosmo Bio Co., Ltd.) was used for the measurement of MMP-1.

The results are shown as the value of the mean value±standard error (n=4 per a group). As the esculetin derivative of the present invention, 6-(β-2-acetamido-2-deoxy-D-glucopyranosyloxy)-7-(N,N-dimethylcarbamoyloxy)coumarin [Ib-2] was used.

Figure 1:
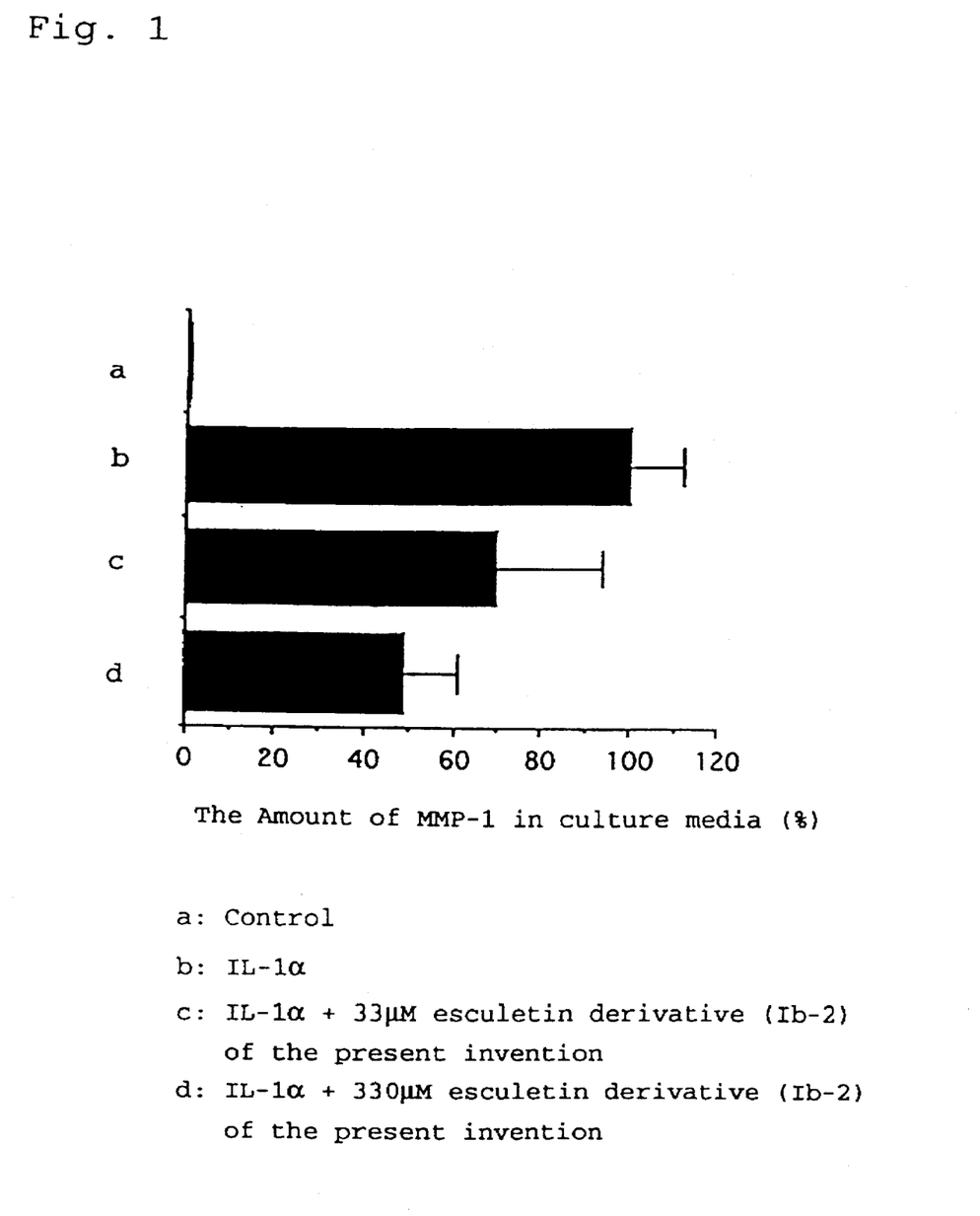
FIG. 1 is a graph showing function to inhibit production of interstitial collagenase (MMP-1) in rabbit cartilage organ culture system. See Example 14.

The results are shown in FIG. 1. The abscissa is the percentage of the amounts of MMP-1 produced by adding both IL-1α and the compound to be tested as compared to the amounts of MMP-1 produced by the addition of IL-1α alone. When neither IL-1α nor the compound to be tested were added as a control test, MMP-1 was hardly produced. The addition of IL-1α induced a significant increase of MMP-1 released in a culture medium, whereas the esculetin derivative of the present invention [Ib-2] reduced the amounts of MMP-1 under IL-1α stimulated condition.

The results in Example 14 show that the esculetin derivative of the present invention is useful as a matrix metalloproteinase inhibitor, and further as an agent for treating an arthropathy.

Example 15

Pharmacokinetic Analysis in Mouse FHC Model
(1) Preparation of Model Mice

The model mice were prepared in accordance with the method described in D. A. Willoughby et al., Agents Actions, vol. 38, pp. 126 to 134, 1993.

The left and right femoral head cartilages (FHC) were sterilely excised from S. D. male rats in a clean bench. The excised FHC's were washed with a Ham F-12 culture medium containing antibiotics and the wet weight was measured. Then, the FHC's were wrapped in two cotton sheets (about 1 cm×1 cm) and cooled with ice in the culture medium for storage until implantation. The FHC's were implanted sterilely under the dorsal skin of BALB/C female mice whose dorsal regions were shaved. The incisions were stitched, and then completely sealed with surgical adhesive (Toa Gosei, Japan).
(2) Pharmacokinetic analysis in FHC after administering esculetin and 6-(β-2-acetamido-2-deoxy-D-glucopyranosyloxy)- 7-(N,N-dimethylcarbamoyloxy) coumarin [Ib-2]

The above mouse FHC model were used to pharmacokinetically compare esculetin and the esculetin derivative [Ib-2] of the present invention. Esculetin (187 mg/kg) and an equimolar amount, i.e., 534 mg/kg, of the esculetin derivative [Ib-2] of the present invention were administered orally three days after the implantation of the FHC. The FHC's were periodically removed and digested with papain. Then, an amount of the compounds taken up in the FHC was analyzed by high performance liquid chromatography. In the above experiments, three mice were used for each group.

Figure 2:
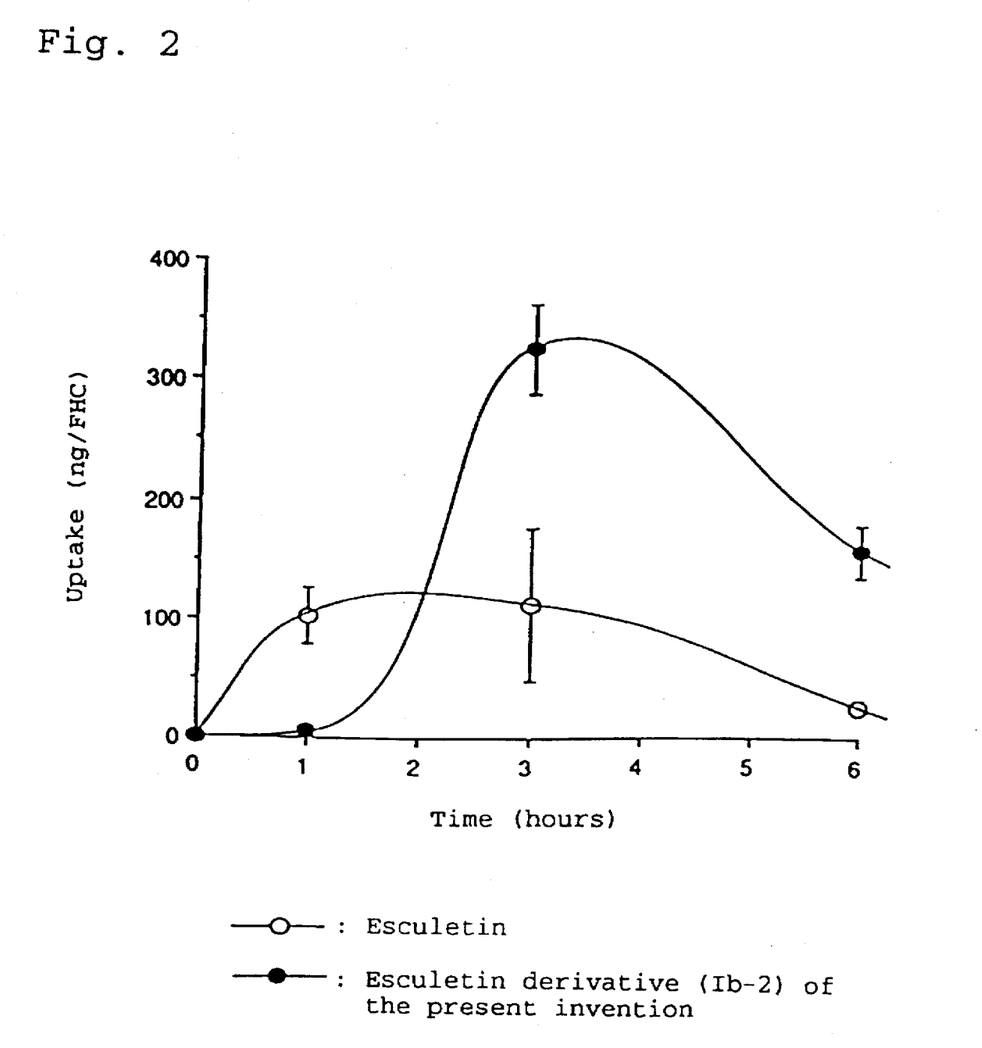
FIG. 2 is a graph showing the amounts of the compound of the present invention and esculetin taken up in the femoral head cartilage (FHC) in a mouse FHC model. See Example 15.

The results are shown in FIG. 2. The amounts of the esculetin derivative [Ib-2] of the present invention taken up by administering [Ib-2] are shown by the closed circles (●) and the amounts of esculetin taken up by administering esculetin are shown by the open circles (o) in FIG. 2. As shown in FIG. 2, the esculetin derivative [Ib-2] of the present invention is taken up and retained in the FHC for a long time in a higher concentration as compared to esculetin.

As explained, the novel esculetin derivative of the present invention or a salt thereof exhibits the function to inhibit production of matrix metalloproteinases. For the amount taken up, affinity and local retention in the cartilage matrix, the novel esculetin derivative of the present invention or a salt thereof is superior to esculetin, 4-alkylesculetin or the like. Further, the novel esculetin derivative of the present invention or a salt thereof is high efficiently used in the body and has low toxicity. Accordingly, the esculetin derivative of the present invention or a salt thereof is extremely useful as an active ingredient in pharmaceutical compositions, particularly matrix metalloproteinase inhibitors, or for the treatment of infiltration and metastasis of cancer, pulmonary emphysema, bone resorption, arthropathy, such as rheumatoid arthritis, osteoarthritis, periarthritis humeroscapularis, shoulder-arm-neck syndrome, lumbago, or the like, corneal ulcer, wound, granuloma, periodontosis, vesicular exanthem, glomerular nephritis, or the like.

Although the present invention has been described with reference to specific embodiments, various changes and modifications obvious to those skilled in the art are deemed to be within the spirit, scope, and concept of the invention.

We claim:

1. A compound of the formula (I):

wherein $R^1$ and $R^2$ are, independently, —CON($R^4$)$R^5$, or a monosaccharide, or acylated monosaccharide group, with the proviso that at least one of $R^1$ and $R^2$ is —CON($R^4$)$R^5$, and $R^4$ and $R^5$ together with the nitrogen atom attached thereto form a 3- to 7-membered saturated cycloaliphatic amino group optionally containing one or more heteroatoms in addition to the nitrogen atom, and $R^3$ is a hydrogen atom, or a hydroxyl, alkyl, aryl, aralkyl, or —COOR$^8$ group, and $R^3$ is at 3- or 4-position, and $R^8$ is a hydrogen atom or an alkyl group, or a salt thereof.

2. A compound according to claim 1, wherein the monosaccharide group is a hexose or pentose group.

3. A compound according to claim 2, wherein the monosaccharide group is a group of mannose, allose, altrose, talose, glucose, galactose, idose, gulose, fructose, rhamnose, fucose, glucosamine, N-acylglucosamine, galactosamine, N-acylgalactosamine, N-acylmuramic acid, glucuronic acid, gulonic acid, iduronic acid, ascorbic acid, mannitol, sorbitol, arabinose, xylose, ribose, or deoxyribose.

4. A compound according to claim 1, wherein $R^4$ and $R^5$ are, independently, a hydroxyl group, an alkyl group of 1 to 4 carbon atoms, an aryl group of 6 to 12 carbon atoms, or an alkyl group of 1 to 4 carbon atoms substituted with an aryl group of 6 to 12 carbon atoms, or $R^4$ and $R^5$ together with the nitrogen atom attached thereto form an alkyleneamino group optionally containing one or more heteroatoms in addition to the nitrogen atom, and $R^3$ is a hydrogen atom, or a hydroxyl group, an alkyl group of 1 to 4 carbon atoms, an aryl group of 6 to 12 carbon atoms, an alkyl group of 1 to 4 carbon atoms substituted with an aryl group of 6 to 12 carbon atoms, or —COOR$^8$ group, and $R^8$ is a hydrogen atom or an alkyl group of 1 to 4 carbon atoms.

5. A compound according to claim 1, wherein $R^1$ is —CON(CH$_3$)$_2$, —CON(C$_2$H$_5$)$_2$, or morpholino group, $R^2$ is —CON(CH$_3$)$_2$, —CON(C$_2$H$_5$)$_2$, a morpholino group, an N-acetyl glucosamine group, a 6-pivaloylated N-acetyl glucosamine group, a glucose group, a galactose group, an N-acetyl galactosamine group, or a glucuronic acid group, and R$^3$ is a hydrogen atom, or a methyl or —COOCH$_3$ group.

6. A compound according to claim 1, wherein R$^1$ is —CON(CH$_3$)$_2$, —CON(C$_2$H$_5$)$_2$, a morpholino group, an N-acetyl glucosamine group, a 6-pivaloylated N-acetyl glucosamine group, a glucose group, a galactose group, an N-acetyl galactosamine group, or a glucuronic acid group, R$^2$ is —CON(CH$_3$)$_2$, —CON(C$_2$H$_5$)$_2$, or morpholino group, and R$^3$ is a hydrogen atom, or a methyl or —COOCH$_3$ group.

7. A process for manufacturing an esculetin compound of formula (I):

wherein R$^1$ and R$^2$ are, independently, —CON(R$^4$)R$^5$, or a monosaccharide, or acylated monosaccharide group, with the proviso that at least one of R$^1$ and R$^2$ is —CON(R$^4$)R$^5$, and R$^4$ and R$^5$ are, independently, a hydroxyl, alkyl, aryl, or aralkyl group, or R$^4$ and R$^5$ together with the nitrogen atom attached thereto form a 3- to 7-membered saturated cycloaliphatic amino group optionally containing one or more heteroatoms in addition to the nitrogen atom, and R$^3$ is a hydrogen atom, or a hydroxyl, alkyl, aryl, aralkyl, or —COOR$^8$ group, and R$^3$ is at 3- or 4-position, and R$^8$ is a hydrogen atom or an alkyl group, or the salt thereof, comprising reacting a compound of the formula (XI)

wherein R$^3$ has the same meaning as above, a compound of the formula (II)

wherein R$^3$ has the same meaning as above and R$^6$ is a monosaccharide or acylated monosaccharide group, or a compound of the formula (II')

wherein R$^3$ and R$^6$ have the same meanings as above, with a compound of the formula (X)

R$^5$(R$^4$)NCOX                    (X)

wherein R$^4$ and R$^5$ have the same meanings as above and X is a halogen atom.

8. A pharmaceutical composition comprising a compound of the formula (I):

wherein R$^1$ and R$^2$ are, independently, —CON(R$^4$)R$^5$, or a monosaccharide, or acylated monosaccharide group, with the proviso that at least one of R$^1$ and R$^2$ is —CON(R$^4$)R$^5$, and R$^4$ and R$^5$ are, independently, a hydroxyl, alkyl, aryl, or aralkyl group, or R$^4$ and R$^5$ together with the nitrogen atom attached thereto form a 3- to 7-membered saturated cycloaliphatic amino group optionally containing one or more heteroatoms in addition to the nitrogen atom, and R$^3$ is a hydrogen atom, or a hydroxyl, alkyl, aryl, aralkyl, or —COOR$^8$ group, and R$^3$ is at 3- or 4-position, and R$^8$ is a hydrogen atom or an alkyl group, or a pharmaceutically acceptable salt thereof, and a pharmaceutically acceptable carrier.

9. A pharmaceutical composition according to claim 8, which is a matrix metalloproteinase.

10. A pharmaceutical composition according to claim 8, which is an agent for treating an arthropathy.

11. A method for treatment of a disease relating to a matrix metalloproteinase comprising administering to a mammal in need therof the compound according to claim 1 in an amount effective for a disease relating to the matrix metalloproteinase.

12. A process according to claim 7, wherein the monosaccharide group is a hexose or pentose group.

13. A process according to claim 11, wherein the monosaccharide group is a group of mannose, allose, altrose, talose, glucose, galactose, idose, gulose, fructose, rhamnose, fucose, glucosamine, N-acylglucosamine, galactosamine, N-acylgalactosamine, N-acylmuramic acid, glucuronic acid, gulonic acid, iduronic acid, ascorbic acid, mannitol, sorbitol, arabinose, xylose, ribose, or deoxyribose.

14. A process according to claim 7, wherein R$^4$ and R$^5$ are, independently, a hydroxyl group, an alkyl group of 1 to 4 carbon atoms, an aryl group of 6 to 12 carbon atoms, or an alkyl group of 1 to 4 carbon atoms substituted with an aryl group of 6 to 12 carbon atoms, or R$^4$ and R$^5$ together with the nitrogen atom attached thereto form an alkyleneamino group optionally containing one or more heteroatoms in addition to the nitrogen atom, and R$^3$ is a hydrogen atom, or a hydroxyl group, an alkyl group of 1 to 4 carbon atoms, an aryl group of 6 to 12 carbon atoms, an alkyl group of 1 to 4 carbon atoms substituted with an aryl group of 6 to 12 carbon atoms, or —COOR$^8$ group, and R$^8$ is a hydrogen atom or an alkyl group of 1 to 4 carbon atoms.

15. A process according to claim 7, wherein R$^1$ is —CON(CH$_3$)$_2$, —CON(C$_2$H$_5$)$_2$, or morpholino group, R$^2$ is —CON(CH$_3$)$_2$, —CON(C$_2$H$_5$)$_2$, a morpholino group, an N-acetyl glucosamine group, a 6-pivaloylated N-acetyl glucosamine group, a glucose group, a galactose group, an N-acetyl galactosamine group, or a glucuronic acid group, and R$^3$ is a hydrogen atom, or a methyl or —COOCH$_3$ group.

16. A process according to claim 7, wherein R$^1$ is —CON(CH$_3$)$_2$, —CON(C$_2$H$_5$)$_2$, a morpholino group, an N-acetyl glucosamine group, a 6-pivaloylated N-acetyl glucosamine group, a glucose group, a galactose group, an N-acetyl galactosamine group, or a glucuronic acid group, R$^2$ is —CON(CH$_3$)$_2$, —CON(C$_2$H$_5$)$_2$, or morpholino group, and R$^3$ is a hydrogen atom, or a methyl or —COOCH$_3$ group.

* * * * *

UNITED STATES PATENT AND TRADEMARK OFFICE
CERTIFICATE OF CORRECTION

PATENT NO.    : 5,731,293
DATED         : March 24, 1998
INVENTOR(S)   : Koju Watanabe, Koichi Niimura, Toru Yamazaki, Hiroshi Maruoka It is certified that error(s) appears in the above-identified patent and that said Letters Patent is hereby corrected as shown below:

Column 25, line 15, before "formula" insert --the--.

Column 26, line 28, delete "therof" and insert therefor --thereof--.

Signed and Sealed this

Twenty-ninth Day of September, 1998

Attest:

*Bruce Lehman*

BRUCE LEHMAN

*Attesting Officer*       *Commissioner of Patents and Trademarks*